United States Patent [19]

van der Schoot

[11] Patent Number: 4,775,051
[45] Date of Patent: Oct. 4, 1988

[54] APPARATUS FOR SORTING AND REMOVING UNDESIRABLE OBJECTS FROM A FEED BELT CONVEYOR

[75] Inventor: Jelle van der Schoot, Aalten, Netherlands

[73] Assignee: Staalkat B.V., Aalten, Netherlands

[21] Appl. No.: 91,283

[22] Filed: Aug. 28, 1987

Related U.S. Application Data

[63] Continuation of Ser. No. 752,355, Jul. 3, 1985, abandoned.

[51] Int. Cl.⁴ ............................................. A01K 43/08
[52] U.S. Cl. .................................. 209/510; 198/369; 209/513; 209/656; 209/698
[58] Field of Search .................................. 209/510–513, 209/539, 552, 656, 657, 698, 651, 653, 707, 912, 918, 922, 917, 925; 198/369, 463.4, 722, 779

[56] References Cited

U.S. PATENT DOCUMENTS

| | | | |
|---|---|---|---|
| 1,764,663 | 6/1930 | Voigt | 198/369 |
| 1,960,231 | 5/1934 | Cooper | 209/511 |
| 2,461,308 | 2/1949 | Brown | 209/924 |
| 2,993,592 | 7/1961 | Mumma | 209/510 |
| 3,031,077 | 4/1962 | Mumma et al. | 209/511 |
| 3,254,763 | 6/1966 | Surber | 209/698 |
| 3,278,025 | 10/1966 | Willsey et al. | 209/511 |
| 3,948,765 | 4/1976 | Anschutz | 209/513 |
| 4,164,291 | 8/1979 | Carlow | 209/942 |
| 4,356,920 | 11/1982 | van der Schoot | 209/513 |
| 4,426,074 | 1/1984 | Fischer | 198/369 |
| 4,519,505 | 5/1985 | Thomas | 209/513 |

FOREIGN PATENT DOCUMENTS

| | | | |
|---|---|---|---|
| 107788 | 7/1967 | Denmark | 209/510 |
| 0092989 | 2/1987 | European Pat. Off. | |
| 562107 | 10/1932 | Fed. Rep. of Germany | 209/510 |
| 3138748 | 4/1983 | Fed. Rep. of Germany | 209/510 |

Primary Examiner—Robert B. Reeves
Assistant Examiner—Donald T. Hajec
Attorney, Agent, or Firm—Scully, Scott, Murphy & Presser

[57] ABSTRACT

An apparatus for sorting and removing undesirable objects from a feed belt conveyor which passes an inspection station, while downstream of the inspection station there is arranged a "trapdoor" and subsequently a discharge conveyor. The undesirable objects can be discharged through the trapdoor, which undesirable objects can be defined as such upstream of the trapdoor by human or automatic detection. The location of the objects in question can for instance be defined by a "tracking" memory (shift register) and remains known at least as far as the trapdoor. In an apparatus more particularly adapted for processing vulnerable objects, such as eggs, the feed belt conveyor and the discharge belt conveyor are substantially aligned, there being arranged at least adjacent the trapdoor disposed between the belts, a turnstile, a chain having carriers (FIG. 2) or the like.

15 Claims, 2 Drawing Sheets

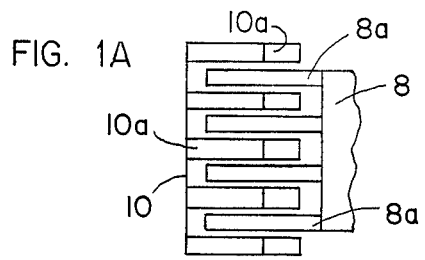
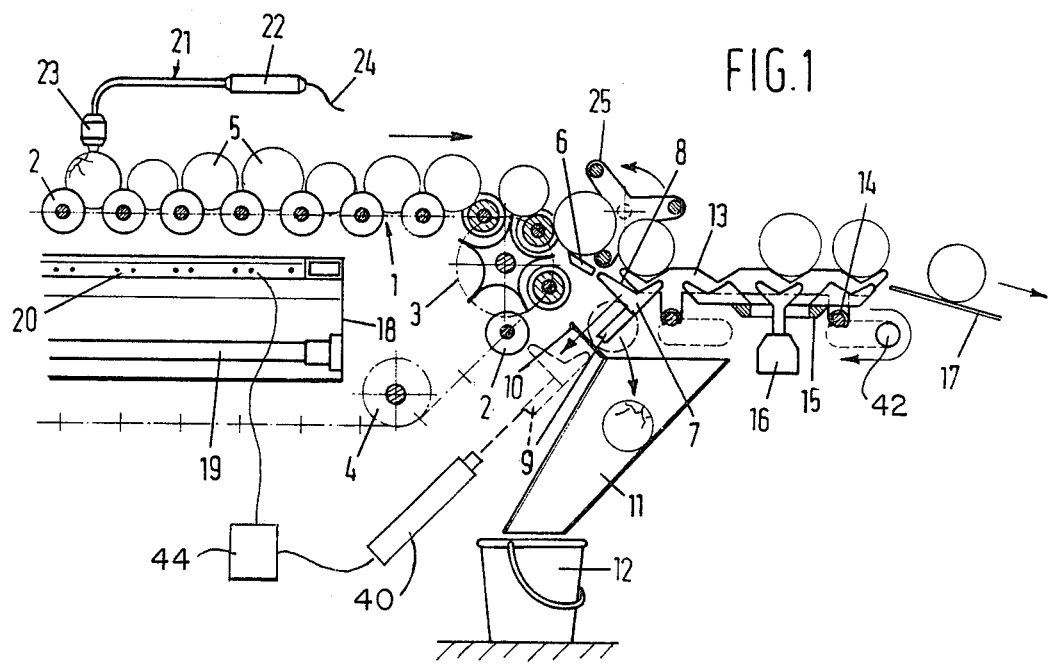
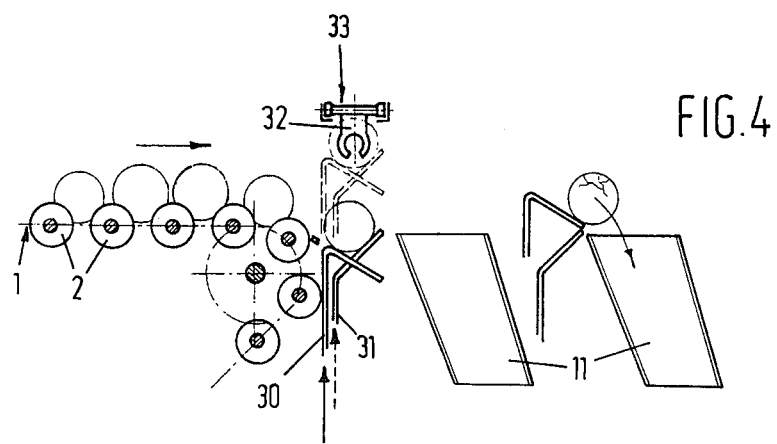

APPARATUS FOR SORTING AND REMOVING UNDESIRABLE OBJECTS FROM A FEED BELT CONVEYOR

This application is a continuation of application Ser. No. 752,355, filed July 3, 1985, now abandoned.

BACKGROUND OF THE INVENTION

The present invention relates to an apparatus for sorting and removing undesirable objects from a feed belt conveyor, which belt passes an inspection station, while a downstream of the inspection station there is arranged a "trapdoor" and subsequently a discharge conveyor, enabling the undesirable objects to be discharged through the trapdoor, which undesirable objects upstream of the trapdoor can be defined as such by human or automatic detection, while the location of the objects in question can for instance be determined by a "tracking" memory (shift register) and remains known at least as far as the trapdoor.

Such an apparatus is disclosed in European patent application No. 0 092 989. In this prior art apparatus for sorting potatoes, use is made of a plurality of spaced apart, superimposed belt conveyors. Underneath the discharge end of the feed belt conveyor, there are disposed a plurality of flaps operable by cylinders. As soon as an undesirable potato passes the discharge end, the flap is moved outwardly, so that the undesirable potato falls onto a cross-conveyor disposed above the discharge belt conveyor. When the flap is not operated, the good potatoes will fall directly downwardly onto the longitudinally arranged discharge conveyor.

Such an apparatus is entirely unsuitable for sorting and removing eggs and the like vulnerable products.

SUMMARY OF THE INVENTION

It is an object of the present invention to eliminate the above drawback.

To this effect an apparatus of the above described type adapted in particular for processing vulnerable objects, such as eggs, is characterized in that the feed belt conveyor and the discharge belt conveyor are substantially aligned, and at least adjacent the "trapdoor" disposed between the said belts, there is arranged a turnstile, a chain having carriers (FIG. 2) or the like. As a result, a "soft" treatment of the good objects is ensured, while also the undesirable objects are gently removed from the transport path.

By arranging a weighing element downstream of the "trapdoor", a very short sorting apparatus can be obtained, where the undesirable objects are removed already before the weighing.

In a further elaboration of the present invention, the "trapdoor" may comprise a vertically reciprocatable fork-shaped member whose prongs during their movement can pass along the teeth of a guideplate arranged at an acute angle to the vertical. The downstream end of the guideplate may be fixedly connected to a discharge trough.

A different embodiment of the "trapdoor" may comprise a flap disposed in the discharge path for the eggs, which flap is rotatably attached to a frame or the like at the downstream end.

Also the "trapdoor" may consist of two independently vertically movable elements, the top ends of which are designed in such a manner that in the lowest mutual position they form a carrier for the eggs, and a "trapdoor" in an elevated position of one of the movable elements.

It has been experimentally found that the apparatus according to the present invention enables an inspection twice as quick, while the operator gets less tired.

In a further elaboration of the present invention, there may be arranged above the vertically movable elements, a conveying system having grippers, as described in Dutch Pat. No. 166,658, corresponding to U.S. Pat. No. 4,068,882.

The further transport, downstream of the "trapdoor", can take place by means of a "hare's jump" system, a double chain having carrier elements or another conveying element.

Besides, as known per se, guideplates may be arranged between the various conveying elements disposed in the path of motion of the eggs.

BRIEF DESCRIPTION OF THE DRAWING

Some embodiments of the apparatus for sorting and removing undesirable eggs from a feed belt conveyor will now be described, by way of example, with reference to the accompanying drawings, in which:

FIG. 1 is a diagrammatic side view of an apparatus for sorting and removing undesirable eggs from a feed belt conveyor;

FIG. 1A is a schematic view of a part of the apparatus of FIG. 1;

FIGS. 3 and 4 show similar view as FIG. 2, but of a third, and a fourth, embodiment respectively.

DETAILED DESCRIPTION OF THE PREFERRED EMBODIMENTS

Figure 2:
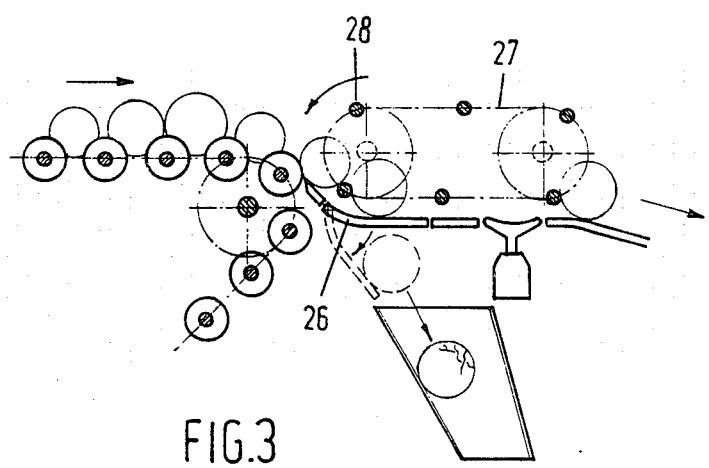
FIG. 2 is a corresponding view of a part of a different apparatus for sorting and removing undesirable eggs from a belt conveyor.

As shown in the drawings, wherein the same parts are indicated by the same reference numerals, an apparatus for sorting and removing undesirable eggs from a belt conveyor comprises an only partly shown belt conveyor 1 having rollers 2, which endless belt conveyor is passed about a chain wheel 3. At the lower end there is provided a diagrammatically shown belt conveyor support wheel 4. Downstream of the chain wheel 3, through which eggs 5 are transported in the direction indicated by an arrow, there is provided a guideplate 6 with a superimposed turnstile 25 and subsequently a trapdoor or trap element 7.

With particular reference to FIGS. 1 and 1A, the trap element 7 is designed at the top as a fork-shaped carrier 8 having a plurality of prongs or teeth 8a. Carrier is attached to the one end of a rod 9 whose other end is operated by a piston-and-cylinder assembly 40. The fork-shaped carrier 8 with the rod 9 are movable in the direction indicated by an arrow along a guideplate 10 consisting of teeth, shown at 10a in FIG. 1A. Guideplate 10 is connected at its one end to a trough 11, under which there is arranged a receptacle 12, in the present case a bucket.

Downstream of the trap element 7 there is provided a conveying element 13 adapted to perform a reciprocating and an up and down movement in the form of a "hare's jump". In the drawing, dotted lines indicate the movement patterns of two mounting shafts 14 of the conveying element 13 relatively to the frame, not shown. Any suitable drive means, schematically represented at 42, may be connected to conveying element 13 to drive that element both upward and downward. As further shown in the drawing, the frame has a recess 15 through which extends the top end of a scale 16. The scale may be of the type as described in U.S. Pat. No. 3,980,147 of applicants.

Downstream of the conveying element 13 there is arranged a guideplate 17.

In order to detect the undesirable eggs, there is arranged underneath the top part of the belt conveyor 1, a bin 18 having a light source 19 as well as a coil system 20 feeding a "tracking" memory, schematically shown at 44.

The apparatus furthermore comprises a pointer 21 having a grip 22. The one end of the pointer is provided with a head 23 having a switch and an amplifier. The other end of the pointer is fitted with a conductor 24 for connection to a current source, not shown.

The details of such an apparatus are described in Dutch patent application No. 7707946 and the corresponding U.S. Pat. No. 4,164,291.

It will be clear that the operation of the piston-and-cylinder assembly 40 or similar driving mechanism operating the rod 9 of the trap element 7, is controlled by the "tracking" memory 44 which is fed by the coil system 20.

The operation of the apparatus, after the above, seems obvious. When the operator during the passage of the eggs along the top of the receptacle or bin 18 having a light source 19 detects an undesirable egg, he indicates this with the head 23 of the pointer 21. The signal produced is taken up by one of the coils 20 in the tracking memory 44 so that, when the further transported egg reaches the trap element 7, this is operated and moved to the position shown in dashed lines, so that the egg is discharged. As shown in FIG. 1, the eggs are moved from the belt conveyor 1 via the guideplate 6 by means of the turnstile 25 to the trap element 7. When the egg need not be removed, the trap element remains in the position indicated in full lines, so that the egg can be further transported by means of the conveying element 13 towards the scale 16 and subsequently can be discharged via the guideplate 17.

As described above, the trap element 7 serves as an ejector means and is moveable between a first position, wherein the ejector means 7 supports the food articles for movement between conveyors 1 and 13, and a second position, wherein the ejector means 7 guides the food articles toward trough 11; and turnstile 25 comprises article moving means, located above ejector means 7, to guide the food articles onto the ejector means 7.

The article moving means preferably forms a moveable pocket with ejector means so that only one article at a time is on that ejector means 7. Also, piston and cylinder 40 comprises drive means, connected to ejector means 7, to move the guideplate between the above-mentioned first and second positions; and tracking means 44 comprises control means, connected to coil system 20 to receive a control signal therefrom, and also connected to piston unit 40 to move ejector means 7 from its first position to its second position when an undesirable article is on the ejector means 7, to carry that undesirable article to trough 11.

The diagrammatic representation of a second embodiment only partly shown in FIG. 2 differs from the apparatus shown in FIG. 1 in that the trap element here consists of a flap 26 connected at the upstream end rotatably to a frame, not shown. Furthermore, instead of the conveying element 13 and the turnstile 25, use is made herein of a conveying system comprising a pair of chains 27 between which there are arranged carrier elements 28.

Figure 3:
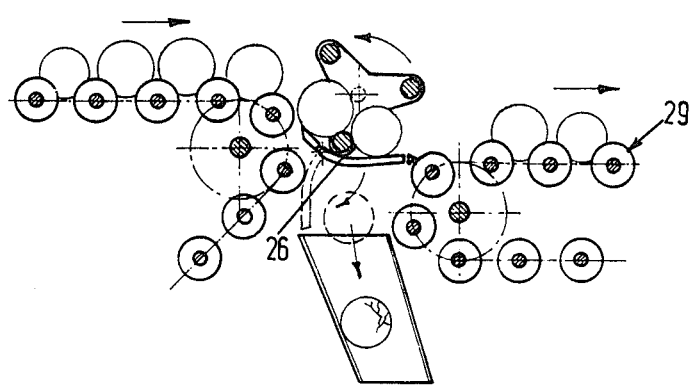

The third embodiment shown in FIG. 3 similarly as represented in FIG. 2, comprises in the same manner as shown in FIG. 2, a flap 26 connected at its upstream end rotatably to a frame. Above the flap there is arranged similarly as in the embodiment shown in FIG. 1, a turnstile 25. Downstream of the flap, there is provided subsequently a discharge belt conveyor 29, which may be designed similarly as the belt conveyor 1.

The fourth embodiment shown in FIG. 4 comprises a trap element essentially consisting of two independently vertically movable wire-shaped portions 30, 31. The top ends of said portions are bent in such a manner that they form carriers for the eggs supplied in the position shown in full lines. If an undesirable egg is supplied, the wire-shaped portion 30 is lifted, so that the portions 30, 31 reach the position diagrammatically shown at the right beside FIG. 4, so that the undesirable egg rolls into the trough 11.

When, on the other hand, a good egg reaches the trap element consisting of portion 30, 31, then the two portions are jointly lifted into the position shown in dashed lines. In the latter position, the egg is then disposed between the gripper arms of a conveying system 33 having carriers 32. Such a conveying system, as well as a similar vertical conveying element are described in U.S. Pat. No. 4,068,882.

Although four embodiments have been described in the above, this is not a limitative enumeration of possible embodiments. Many variants or combinations are possible within the scope of the present invention.

What I claim is:

1. Apparatus for handling food articles, comprising:
   conveyor means for carrying food articles forward along a path, the conveyor means including
   (i) a feed conveyor for carrying the food articles along a first section of the path, and
   (ii) a discharge conveyor, located forward of and spaced from the feed conveyor, for carrying the food articles further forward along a second section of the path, the second section being substantially aligned with the first section;
   inspection means located adjacent the feed conveyor for identifying undesirable articles thereon and for generating a control signal in response to identifying an undesirable article; and
   a receptacle means located adjacent the conveyor means for receiving undesirable articles;
   the conveyor means further including
   (iii) moveable ejector means located between the feed and discharge conveyors, and moveable between a first position, wherein the ejector means supports the food articles for movement between the feed and discharge conveyors, and a second position, wherein the ejector means guides the food articles toward the receptacle means,
   (iv) article moving means located above the ejector means to guide the food articles onto the ejector means from the feed conveyor so that only one article at a time is on the ejector means,
   (v) drive means connected to the ejector means to move the ejector means between the first and second positions, and
   (vi) control means connected to the inspection means to receive the control signal therefrom, and connected to the drive means to actuate the drive means in response to receiving said control signal to move the ejector means from the first position to the second position when an undesirable article is on the ejector means, to carry the undesirable article out of said path and to the receptacle means.

2. Apparatus according to claim 1 further comprising means located along the second section of the path to weigh the food articles.

3. Apparatus according to claims 1 or 2, wherein:
the receptacle means includes an upwardly rearwardly extending guideplate having a plurality of spaced apart teeth;
the ejector means includes a plurality of spaced apart prongs to support the food articles as they move from the feed conveyor to the discharge conveyor;

4. Apparatus according to claim 3, wherein:
the receptacle means further includes a discharge trough for collecting undesirable articles; and
the guideplate is connected to the discharge trough and guides the undesirable articles thereto.

5. Apparatus according to claims 1 or 2, wherein the discharge conveyor includes:
a carrier to hold and carry the food articles; and
drive means to reciprocate the carrier both foward and rearward and upward and downward.

6. Apparatus according to claims 1 or 2, wherein the article moving means includes:
rotary means supported for movement above the ejector means; and
a plurality of bars connected to the rotary means for movement therewith, to engage the food articles and guide the food articles onto the ejector means.

7. Apparatus according to claims 1 or 2, wherein the article moving means includes:
rotary means supported for movement above the ejector means; and
a plurality of rods connected to the rotary means for movement therewith, to engage the food articles and push the food articles along the ejector means and onto the discharge conveyor.

8. Apparatus according to claims 1 or 2, wherein the article moving means includes:
belt means supported for movement above the ejector means; and
a plurality of bars connected to the belt means for movement therewith, to engage the food articles and push the food articles along the ejector means and onto the discharge conveyor.

9. Apparatus according to claim 1 or 2, wherein the article moving means includes:
belt means supported for movement above the ejector means; and
a plurality of rods connected to the belt means for movement therewith, to engage the food articles and push the food articles along the ejector means and onto the discharge conveyor.

10. Apparatus according to claim 1, wherein the ejector means and the article moving means form a moveable pocket for receiving only one food article at a time from the feed conveyor and, when the ejector means is in the first position, moving said one article from the feed conveyor to the discharge conveyor.

11. Apparatus according to claim 1, wherein:
the first position of the ejector means is a stationary position; and
when the ejector means is in said stationary position, the ejector means supports the food articles for movement from a location adjacent the feed conveyor to another location adjacent the discharge conveyor.

12. Apparatus according to claim 1, wherein:
the conveyor means further includes a guideplate located between the feed conveyor and the ejector means to guide the food articles from the feed conveyor and onto the ejector means;
the first positioin of the ejector means is a stationary position;
when the ejector means is in said stationary position, the ejector means extends from a first location closely adjacent the guideplate to a second location closely adjacent the discharge conveyor, and the ejector means supports the food articles for movement between said first and second locations.

13. Apparatus according to claim 1, wherein the control means includes means to delay actuating the drive means after an undesirable article has been identified to allow said undesirable article to move from the feed conveyor and onto the ejector means.

14. Apparatus according to claim 13, wherein:
the food articles comprise eggs; and
the inspection means generates the control signal in response to identifying, cracked eggs.

15. Apparatus for handling food articles comprising:
conveyor means for carrying food articles forward along a path, the conveyor means including
(i) a feed conveyor for carrying the food articles along a first section of the path, and
(ii) a discharge conveyor, located forward of and spaced from the feed conveyor, for carrying the food article further forward along a second section of the path, the second section being substantially aligned with the first section; the discharge conveyor including
(i) a carrier to hold and carry the food articles, and
(ii) drive means to reciprocate the carrier both forward and rearward and upward and downward;
inspection means located adjacent the feed conveyor for identifying undesirable article thereon and for generating a control signal in response to identifying an undesirable article;
a receptacle means located adjacent the conveyor means for receiving undesirable articles;
moveable ejector means located between the feed and discharge conveyors, and moveable between a first position, wherein the ejector means supports the food articles for movement between the feed and discharge conveyors, and a second position, wherein the ejector means guides the food articles toward the receptacle means;
article moving means located above the ejector means to move the food article therealong, when the ejector means is in its first position, from the feed conveyor to the discharge conveyor;
drive means connected to the ejector means to move the ejector means between the first and second positions; and
control means connected to the inspection means to receive the control signal therefrom, and connected to the drive means to actuate the drive means to move the ejector means from the first position to the second position when an undesirable article is on the ejector means to carry the undesirable article out of said path and to the receptacle means.

* * * * *